(12) United States Patent
Lewis

(10) Patent No.: US 6,483,112 B1
(45) Date of Patent: Nov. 19, 2002

(54) HIGH-THROUGHPUT INFRARED SPECTROSCOPY

(76) Inventor: E. Neil Lewis, 2440 Saint Albert Ter., Brookeville, MD (US) 20833

( * ) Notice: Subject to any disclaimer, the term of this patent is extended or adjusted under 35 U.S.C. 154(b) by 0 days.

(21) Appl. No.: 09/353,325

(22) Filed: Jul. 14, 1999

Related U.S. Application Data

(60) Provisional application No. 60/025,800, filed on Aug. 7, 1998, and provisional application No. 60/092,769, filed on Jul. 14, 1998.

(51) Int. Cl.[7] .................................................. G02B 5/23
(52) U.S. Cl. .................. 250/339.02; 250/332; 250/349
(58) Field of Search ............................ 250/339.02, 332, 250/349

(56) References Cited

U.S. PATENT DOCUMENTS

| | | |
|---|---|---|
| 3,737,239 A | 6/1973 | Adams et al. |
| 3,929,398 A | 12/1975 | Bates |
| 4,004,150 A | 1/1979 | Natelson |
| 4,278,538 A | 7/1981 | Lawrence et al. |
| 4,788,428 A | * 11/1988 | Metcalf et al. ............. 250/332 |
| 4,922,092 A | 5/1990 | Rushbrooke et al. |
| 5,029,245 A | 7/1991 | Keranen et al. |
| 5,166,755 A | 11/1992 | Gat |
| 5,244,630 A | 9/1993 | Khalil et al. |
| 5,379,065 A | 1/1995 | Cutts |
| 5,504,332 A | 4/1996 | Richmond et al. |
| 5,508,200 A | 4/1996 | Tiffany et al. |
| 5,528,368 A | 6/1996 | Lewis et al. |
| 5,532,128 A | 7/1996 | Eggers et al. |
| 5,558,231 A | 9/1996 | Weier |
| 5,579,105 A | 11/1996 | Belton et al. |
| 5,589,351 A | 12/1996 | Harootunian |
| 5,615,009 A | 3/1997 | Sakura et al. |
| 5,668,373 A | 9/1997 | Robbat, Jr. et al. |
| 5,675,155 A | 10/1997 | Pentoney, Jr. et al. |
| 5,790,188 A | 8/1998 | Sun |
| 5,828,066 A | 10/1998 | Messerschmidt |
| 5,949,480 A | 9/1999 | Gerhart et al. |
| 6,166,373 A | 12/2000 | Mao |
| 6,211,906 B1 | 4/2001 | Sun |

FOREIGN PATENT DOCUMENTS

| | | |
|---|---|---|
| DE | 28 23 514 A | 5/1978 |
| EP | 0 887 638 A1 | 12/1998 |
| GB | 2 014 300 | 8/1979 |
| GB | 2 315 131 | 1/1998 |
| WO | WO 8905465 A1 | 6/1989 |
| WO | WO 97 13839 | 4/1997 |
| WO | WO 98 15813 | 4/1998 |
| WO | WO 99 02950 | 1/1999 |
| WO | WO 00 60529 | 10/2000 |

OTHER PUBLICATIONS

Akong, M. et al. "High–Throughput Measurement of Intracellular Ca2+ by Fluorescence Imaging of a 96–Well Microtiter Plate", *25th Annual Meeting of the Society for Neuroscience, Society for Neuroscience Abstracts*, 21 (1–3). 1995, 577.

(List continued on next page.)

*Primary Examiner*—Constantine Hannaher
*Assistant Examiner*—Andrew Israel
(74) *Attorney, Agent, or Firm*—Kristofer E. Elbing

(57) ABSTRACT

A spectrometer includes an infrared source, a spectrally selective element, and a cell array. The cell array includes walls that define a number of cavities. The spectrometer also includes an infrared spatial detector responsive to infrared radiation travelling from the infrared source through contents of at least two of the cavities as well as through the spectrally selective element.

75 Claims, 1 Drawing Sheet

OTHER PUBLICATIONS

Frgala, T; Proffitt, RT; Reynolds, CP. "A novel 96–well plate cytotoxicity assay based on fluorescence digital imaging microscopy", *Proceedings of the Eighty–sixth Annual Meeting of the American Association for Cancer Research*, 36 (Mar. 1995).

Geladi, Paul and Grahn, Hans. *Multivariate Image Analysis*. John Wiley and Sons, 1997, pp. vii–xiii, 23–44.

Grant, RL; Acosta, D. "Ratiometric measurement of intracellular pH of cultured cells with BCECF in a fluorescence multi–well Plate reader", *In Vitro Cell Dev Biol Anim*, 33(4) (Apr. 1997), 256–260.

Jansen, EH; Buskens, CA; van den Berg, RH. "Fast Detection of Homogeneous Chemiluminescent Immunoassays with a Sensitive Photoplate", *Journal of Chromatography*, 489 (1989) 245–253.

Schullek, John R; Butler, John H; Ni, Zhi–Jie; Chen, Dawn; Yuan, Zhengyu."A High–Density Screening Format for Encoded Combinatorial Libraries: Assay Miniaturization and Its Application to Enzymatic Reactions". *Analytical Biochemistry*, 246 (1997), 20–29.

\* cited by examiner

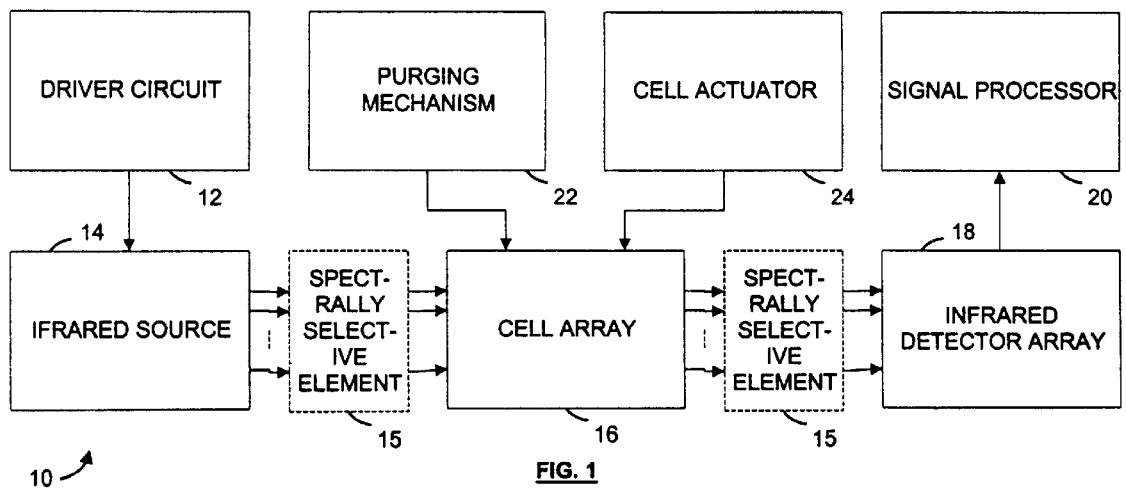
FIG. 1
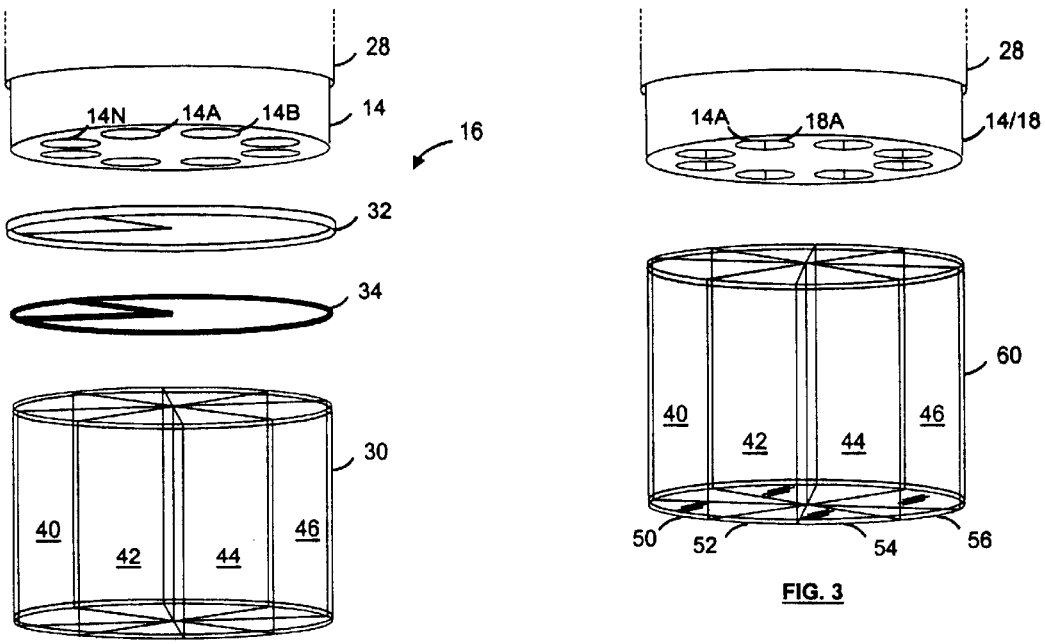
FIG. 2
FIG. 3
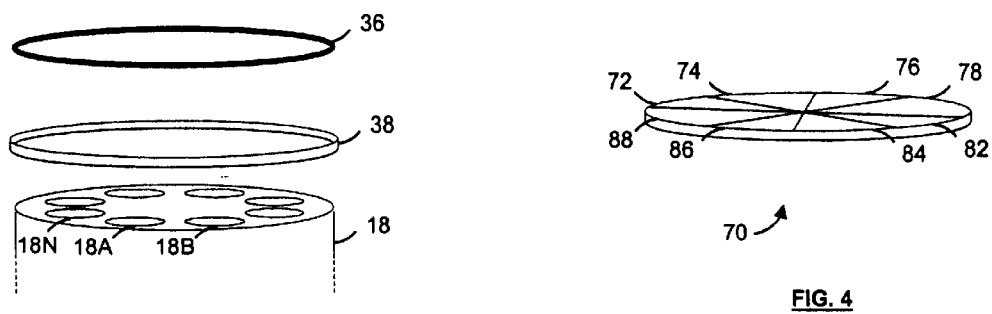
FIG. 4

HIGH-THROUGHPUT INFRARED SPECTROSCOPY

CROSS-REFERENCE TO RELATED APPLICATIONS

This application claims the benefit under 35 U.S.C. 119(e) of U.S. provisional application No. 60/092,769 filed on Jul. 14, 1998 and of U.S. provisional application No. 60/095,800 filed on Aug. 7, 1998, both of which are herein incorporated by reference.

FIELD OF THE INVENTION

This invention relates to high-throughput infrared spectrometers and high-throughput infrared spectroscopic methods.

BACKGROUND OF THE INVENTION

Single-beam infrared spectrometric measurements can be vulnerable to the infrared signature of water vapor and other variations. For this reason, infrared spectrometers are generally calibrated before each set of measurements. This can require purging the instrument, recording a reference spectrum, reopening the instrument, and again purging the instrument with a sample in place, before actual measurements can be taken from the sample.

SUMMARY OF THE INVENTION

Several aspects of the invention are presented in this application. These relate to improvements including improvements to spectrometers and other optical instruments, improvements to vessels for spectrometers, and related methods.

In one general aspect, the invention features a spectrometer that includes an infrared source, a spectrally selective element, and a cell array. The cell array includes walls that define a number of cavities. The spectrometer also includes an infrared spatial detector responsive to infrared radiation travelling from the infrared source through contents of at least two of the cavities as well as through the spectrally selective element.

In preferred embodiments, the spatial infrared detector can be an imaging detector. The imaging detector can be an imaging array implemented using semiconductor manufacturing techniques. A first of the walls can be made of a first material, with a second of the walls being made of second material, and with the first and second materials having significantly different infrared spectral properties. There can be a gasket between the first and second of the walls. The cell array can include at least one infrared-transparent wall. The cell array can include at least one reflective surface. The source and detector can be arranged relative to the reflective surface of the cell array such that infrared radiation is reflected from the source to the detector without passing through any of the walls. The array can be made up of separate vessels. There can be a cover for covering at least one of the cells, or even all of the cells. There can be a gasket between the cover and at least the walls defining one of the cells. At least one of the cells can include a reference substance. A plurality of the cells can be covered by the cover and with the plurality of cells each including a different reference substance. The sample vessel can be a one-piece element with the cells in rigid relationship with each other. At least one of the cells can include a reference substance. A plurality of the cells can each include a different reference substance. The spectrometer can include a purging mechanism for purging a space between at least two of the infrared source, the cell array, and the spatial infrared detector. An actuator can move the cell array. At least one of the cells can include a feed opening. The cells can form part of a process stream conduit.

In another general aspect, the invention features a sample vessel for a spectrometer that includes walls defining a number of cells with at least a first of the walls is being infrared-transparent wall having a first infrared spectral response. In preferred embodiments, a second wall can have a second infrared spectral response different from the first spectral response. At least one of the cells can include a reference substance. The sample vessel can be a one-piece element. At least one of the cells can include a feed opening. The cells can form part of a process stream conduit.

In a further general aspect, the invention features a sample vessel for a spectrometer that includes walls defining a number of cells and at least one reflecting surface located at one or more of the walls and having at least one optical axis crossing the cells. In preferred embodiments, at least one of the cells can include a reference substance. The reflecting element can be deposited on a bottom wall of at least one of the cells in the cell array. The reflecting element can be deposited on a top surface of a bottom wall of at least one of the cells in the cell array. The reflective surface can be made of aluminum. The sample vessel can be a one-piece element The walls can be made of a material having a significant infrared spectrum.

In another general aspect, the invention features an infrared spectrometer that includes a plurality of means for holding substances while being simultaneously located in the spectrometer, means for shining infrared light such that it interacts with the substances held by the plurality of means for holding, means for detecting at least a portion of the infrared light after it has interacted with contents of the means for holding substances, and means for deriving relative spectral information based on signals derived from the plurality of cells detected in the step of detecting. In preferred embodiments, the means for deriving spectral information can include means for capturing an infrared image. The means for shining can be for simultaneously shining infrared light through all of the means for holding, with the means for detecting being for simultaneously detecting infrared light from all of the means for holding. The spectrometer can include means for purging the means for holding before the step of detecting. At least one of the means for holding can include a reference means. The means for deriving can be for determining whether an infrared spectrum of a sample substance in a first of the means for holding is closer to an infrared spectrum of a reference substance in a second of the means for holding or to an infrared spectrum of a reference substance in a third of the means for holding.

In a further general aspect, the invention features an infrared spectroscopy method that includes shining infrared light toward contents of a plurality of cells simultaneously located in an instrument, detecting at least a portion of the infrared light after it has interacted with contents of the cells, and deriving relative spectral information based on signals derived from the plurality of cells detected in the step of detecting. In preferred embodiments, the step of detecting can act on infrared light that has interacted with the plurality of cells by capturing an infrared image. The step of shining can simultaneously shine infrared light through all of the cells and with the step of detecting simultaneously detecting infrared light from all of the cells. A first of the cells can contain a reference substance, with a second of the cells containing a sample substance, and the step of deriving comparing spectral signals from the reference substance and the sample substance. The method can include the step of purging the cells before the step of detecting. The method can include further steps of detecting and deriving for different sample substances in one of the cells and the same reference substance in another of the cells. The method can include further steps of detecting and deriving for different sample substances in one of the cells and a same plurality of different reference substance in others of the cells. One of the cells can include a sample substance and at least a first and a second of the cells can include different reference substances, with the step of deriving determining whether an infrared spectrum of the sample substance is closer to an infrared spectrum of the reference substance in the first cell or to an infrared spectrum of the reference substance in the second cell. One of the cells can include a sample substance and at least a first and second of the cells that include different reference substances, with the step of deriving determining a measure of relative quantities in the sample substance of the reference substance in the first cell and the reference substance in the second cell. The sample can include a product or an intermediate from a reaction and the first and second reference substances can be reagents or intermediates for the reaction. The step of determining can include performing a multivariate spectral analysis. The method can further include changing a process in response to result of the step of determining.

In another general aspect, the invention features a spectrometer that includes a cell array including walls defining a number of cavities, a number of reference samples, each in one of the cavities of the cell array, and a spatial detector responsive to radiation travelling from the infrared source through contents of a plurality of the cavities. In preferred embodiments, the cavities of the cell array that include the reference samples can be sealed, with the spectrometer also including an unsealed cavity for a sample. A processor can be operative to compare spectral information from the number of cavities with spectral information from a sample in a sample cavity.

In a further general aspect, the invention features an optical process monitoring instrument that includes a plurality of process feed conduits, a spatial detector responsive to the feed conduits, and a signal processor responsive to the spatial detector. In preferred embodiments, at least a first of the conduits can be operatively connected to at least a second of the conduits so that contents of the first and second conduits can react.

In another general aspect, the invention features an infrared spectroscopy method that includes shining infrared light toward a plurality of substrate areas simultaneously located in an instrument, detecting at least a portion of the infrared light after it has interacted with substances located on the substrate areas, and deriving relative spectral information based on signals derived from the substances detected in the step of detecting. In preferred embodiments, a first of the areas can support a reference substance, with a second of the areas containing a sample substance, and the step of deriving can compare spectral signals from the reference substance and the sample substance. The method can further include the step of purging a volume between the substrate and apparatus used to perform the step of detecting. One of the plurality of areas can include a sample substance and at least a first and a second of the areas that include different reference substances, and wherein the step of deriving determines whether an infrared spectrum of the sample substance is closer to an infrared spectrum of the reference substance on the first area or to an infrared spectrum of the reference substance on the second area. The step of determining can include performing a multivariate spectral analysis. The method can include a step of initiating a reaction between at least one reagent and the substances on the different areas.

Systems according to the invention can be advantageous in that they can improve the throughput of infrared spectrometers. By providing simultaneous capture of spectra from a library of reference samples at the same time as measurements are taken, spectrometers according to the invention can perform detailed comparisons between a sample and those reference samples in a single acquisition cycle. And by providing a number of sample vessels, a number of measurements can be taken either simultaneously, or in close succession. Such improvements can translate into throughput gains that permit high numbers of samples to be analyzed either in discrete batches or as part of a continuous process.

BRIEF DESCRIPTION OF THE DRAWINGS

FIG. 1 is a block diagram of an infrared spectrometer according to the invention;

FIG. 2 is an exploded perspective view of the source, cell array, and detector of the spectrometer of FIG. 1, FIG. 3 is an exploded perspective view of the source, cell array, and detector for a spectrometer according to FIG. 1 that employs a reflective surface; and FIG. 4 is a perspective view of an immobilizing substrate for use with the spectrometer of FIG. 1.

DETAILED DESCRIPTION OF AN ILLUSTRATIVE EMBODIMENT

Referring to FIGS. 1–2, an infrared spectrometer according to the invention 10 includes an infrared driver circuit 12 having an output operatively connected to an infrared source 14 that provides infrared radiation through a plurality of output paths. The spectrometer also includes a cell array 16 that defines two or more cells that are each located in one of the output paths. An infrared detector array 18 includes a plurality of detector elements each responsive to infrared light transmitted through one of the cells in the cell array, and a signal processor circuit 20 is responsive to the detector array. An spectrally selective element 15 can be provided between the source and the cell array or between the cell array and detector array. A purging mechanism 22 can also be provided to purge spaces between the cell array, the source, and the detector array. An optional actuator 24 can be operatively corrected to move the cell array, the source, and/or the detector array relative to each other.

The source 14 can include one or more sources of infrared light, and may also include one or more collimating or redirecting elements such as optical fibers. Its purpose is to shine radiation though one or more of the cells.

The cell array 16 can include a wall element 30 that defines two or more cells 40, 42, 44, 46 . . . The cell array can include at least one wall, such as a bottom wall 38, that is transparent to infrared radiation (e.g., made of quartz or calcium fluoride). This portion can be sealed to the wall element via a gasket 36, allowing the wall element to be made of a less expensive material that is not transparent in the infrared spectral regions. The cell array 16 can also be made up of a series of separate cell elements, such as a conventional 96-well plate.

The cell array 16 can have a cover 32 that covers some or all of the cells 40, 42, 44, 46. The cover can also be sealed to the wall element 30 by a gasket 34. The cover and/or bottom wall can be affixed to the wall unit temporarily or permanently. Temporary connections can be made with screw threads, bayonet couplings, or other suitable fastening elements. Permanent fixtures can be made using adhesives, welds, or other suitable methods.

The infrared detector array 18 can include a series of individual detectors, which are each aligned with one of the cells, or it can be a two-dimensional imaging array of detectors, such as a charge coupled device (CCD) detector. A single, multiplexed detector may also be used in some embodiments (e.g., a detector coupled with a mirror array, or other multi-element shutter-like device). The principles described in copending. The principles described in this application can be used in connection with the principles described in copending provisional applications entitled DEPTH-RESOLVED INFRARED SPECTROSCOPIC IMAGING ANT) SPECTROSCOPY, Ser. No. 60/091,602 and SPECTROMETRY EMPLOYING MIRROR ARRAYS, Ser. No. 60/091,641, both filed Jul. 2, 1998 and herein incorporated by reference, as well as an application entitled METHODS AND DEVICES FOR VERY RAPID SCAN INTERFEROMETRY, Ser. No. 09/115,211, filed on Jul. 14, 1998, which is also herein incorporated by reference.

The signal processor 20 can be a general-purpose processor programmed with special-purpose software or a special-purpose processor. It can include spectroscopic and other analytic capabilities as well as control capabilities for further elements of the system. Preferably, the signal has sufficient computational capabilities to perform real-time processing, such that its capabilities do not limit spectrometer throughput.

The spectrometer 10 can also include a purging mechanism. This mechanism is constructed to remove air laden with water vapor and/or other contaminants from spaces between the source 14, the cell array 16, and the detector array 18. It can do so by evacuating the spaces or by replacing the contaminants with an infra-red transparent fluid, such as gaseous nitrogen. The purging mechanism can be constructed with a moveable shroud 28 that surrounds the species to be purged, as well as a source of gas or a vacuum pump.

An actuator 24 may also be provided. This actuator can be constructed to move the cell array 16 relative to the source 14 and/or the detector array 18. It can move a cell array into position or change its position relative to the source and/or the detector array.

Referring to FIG. 3, the cell array 16 can also include a reflective surface. This surface can define a number of mirror segments 50, 52, 54, 56 that are each positioned to reflect light from a source element (e.g., 14A) to a deflector element (e.g., 18A) through the contents of one of the cells in the array. Note that the light passes through the sample twice, increasing the amount of interaction with the sample. In one embodiment, the cell array 60 is made up of a plastic material coated with an aluminum coating to define the reflective elements. The cell array can also include a number of separate mirror-coated wells held in a tray or plate.

Referring to FIGS. 1–3, operation of the spectrometer 10 according to the invention begins with by two or more of the cells 40, 42, 44, 46 . . . of the cell array 16 being filled with samples and/or references. This can take place manually or automatically. The purge mechanism 22 can then be used to purge the spaces between the cell array 16, the infrared source 14, and the infrared detector array 18, before the measurement takes place.

The driver circuit 12 then causes in the infrared source 14 to irradiate at least some of the cells. After interaction with the contents of the cells, the infrared detector array acquires a spectral signal and provides it to the signal processor 20, which analyzes the signal.

The cell actuator can move the cell array into place or it can adjust the position of the cell array. By providing a cell actuator to position the cells in the spectrometer, high-throughput automated screening can be accomplished. By changing the position of the cell array and thereby changing the source and/or detector element in the source and detector arrays which services each particular cell, differences between the source elements and/or detector elements can be cancelled. Note that the purge mechanism can purge the six cell array before it is moved into place, and by providing partial sealing of the cells, it may also be possible to pre-purge the reference and background samples in the cell array, so that they do not need to be purged before each measurement.

The reference cells can act as a reference library that can be used repeatedly for successive spectral measurements. In some types of measurements, the spectral reference library can be used to calibrate the machine, while in others the spectrometer will actually gauge the degree of similarity between the sample and known references, or perform other signal manipulations. For example, the system can compare energy levels at different wavelengths with different samples and make determinations based on a degree of similarity between the sample and one or more references. These determinations can be qualitative, (e.g., finding a best match) and/or quantitative. For example, an instrument may be able to determine relative or absolute amounts of component reagents and/or products in a reaction (at timed intervals or after equilibrium has been reached) based on a least-mean-squared (LMS) analysis. It may also be possible for the signal processor to subtract a reference signal from a sample signal, and then analyze the resulting difference signal. In systems with larger cell arrays, the signal processor can employ matrix operations to process a number of samples at a time.

Cells in the array can be simple closed cells, or they can be fed through an opening either from other cells or outside sources. Using two connected cells, an instrument can monitor a reaction in real time, continuously determining relative concentrations of reagents, products, and/or intermediates. The cells may also form parts of process feed lines, such that multiple processes can be monitored in real time. Where processes are related, manipulations within the image processor can be simplified, or the processor can be used to control one variable related to signal values for a first cell based on readings from a second cell. Cells can also be defined in a variety of other ways, such as by compressed air flows, by magnets, or adhesives holding an array of samples in place. Some of the principles of the invention are applicable to other types of optical measurements, such as fluorescence or colorimetry.

Because reference and unknown samples can be processed at the same time, variations between measurements can be minimized. Such variations can arise due to temperature variations, atmospheric conditions, instrument calibration errors, or other variations such as component-related variations.

Referring to FIG. 4, reference and/or unknown samples can also be immobilized on a substrate 70. This substrate includes a number of areas 72, 74, 76, 78, 80, 82, 84, 86 on which different species have been deposited. The different species can be deposited on the substrate directly, or they can be the result of a reaction between one or more reagents deposited on the substrate and one or more reagents applied to the substrate to yield the species to be tested. The substrates can take the form of solid plates or beads, or can employ any other suitable structure.

In one example, so-called combinatorial chemistry techniques are used to generate a number of slightly differing substances to be tested, with each substance occupying one of the areas. The substrate is then introduced in the instrument and its infrared properties can be measured, either alone or in the presence of a reagent, such as an enzyme. By designing the experiment appropriately, the result can indicate which, if any, of the substances has a desirable property, such as a pharmaceutical effect. This technique is applicable to a variety of substances and reagents, from relatively simple molecules to labeled DNA sequences and even larger samples, such as seeds. A sorting mechanism, such as a compressed air source can be used to separate desired samples from undesired samples.

In another example, the technique is applied to spectroscopic composition testing of pharmaceutical dosage units, such as capsules or tablets, during manufacturing. This technique is described more fully in a copending provisional application entitled HIGH-VOLUME ON-LINE SPECTROSCOPIC COMPOSITION TESTING OF MANUFACTURED PHARMACEUTICAL DOSAGE UNITS, filed on Feb. 19, 1999, Ser. No. 60/120,859, and in another copending provisional application having the same title and filed on the same day as this application. Both of these applications are herein incorporated by reference.

The present invention has now been described in connection with a number of specific embodiments thereof However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

What is claimed is:

1. A spectrometer, comprising:
   an infrared source,
   a cell array including a plurality of walls defining a plurality of cavities,
   a spectrally selective element, and
   an infrared spatial detector responsive to infrared radiation traveling from the infrared source through contents of a plurality of the cavities as well as through the spectrally selective element.

2. The spectrometer of claim 1 wherein the spatial infrared detector is an imaging detector.

3. The spectrometer of claim 2 wherein the imaging detector is an imaging array implemented using semiconductor manufacturing techniques.

4. The spectrometer of claim 1 wherein the wherein a first of the walls is made of a first material, wherein a second of the walls is made of second material, and wherein the first and second materials have significantly different infrared spectral properties.

5. The spectrometer of claim 1 wherein the cell array includes at least one infrared-transparent wall.

6. The spectrometer of claim 1 wherein the cell array further includes at least one reflective surface.

7. The spectrometer of claim 1 wherein the array is made up of separate vessels.

8. The spectrometer of claim 1 further including a cover for covering at least one of the cells.

9. The spectrometer of claim 8 wherein the cover covers all of the cells.

10. The spectrometer of claim 8 wherein the at least one of the cells includes a reference substance.

11. The spectrometer of claim 8 wherein a plurality of the cells is covered by the cover and wherein the plurality of cells each includes a different reference substance.

12. The spectrometer of claim 1 wherein the cell array is a one-piece element with the cells in rigid relationship with each other.

13. The spectrometer of claim 1 wherein at least one of the cells includes a reference substance.

14. The spectrometer of claim 1 wherein a plurality of the cells each includes a different reference substance.

15. The spectrometer of claim 1 wherein at least one of the cells includes a feed opening.

16. The spectrometer of claim 1 wherein the cells form part of a process stream conduit.

17. The spectrometer of claim 1 further including at least one optical fiber in an optical path between the infrared source and the infrared spatial detector.

18. The spectrometer of claim 1 further including a plurality of optical fibers that are each located in an optical path between at least a portion of the infrared source and at least one element of the infrared spatial detector.

19. A sample vessel for a spectrometer, comprising:
    a plurality of walls defining a plurality of cells, wherein at least a first of the walls is an infrared-transparent wall having a first infrared spectral response, and
    wherein each of at least a plurality of the cells includes a different reference substance.

20. The vessel of claim 19 further including a second wall having a second infrared spectral response different from the first spectral response.

21. The spectrometer of claim 19 wherein the sample vessel is a one-piece element.

22. The spectrometer of claim 19 wherein at least one of the cells includes a feed opening.

23. The spectrometer of claim 19 wherein the cells form part of a process stream conduit.

24. A sample vessel, for a spectrometer comprising:
    a plurality of walls defining a plurality of cells, and
    at least one reflecting surface located at one or more of the walls and having at least one optical axis crossing the plurality of cells.

25. The vessel of claim 24 wherein at least one of the cells includes a reference substance.

26. The vessel of claim 24 wherein the reflecting element is deposited on a bottom wall of at least one of the cells in the cell array.

27. The spectrometer of claim 24 wherein the sample vessel is a one-piece element.

28. The spectrometer of claim 24 wherein the walls are made of a material having a significant infrared spectrum.

29. An infrared spectrometer, comprising:
    a plurality of means for holding substances while being simultaneously located in the spectrometer,
    means for shining infrared light such that it interacts with the substances held by the plurality of means for holding,
    means for detecting at least a portion of the infrared light after it has interacted with contents of the means for holding substances, and
    means for deriving spectral information based on signals derived from the plurality of cells detected in the step of detecting.

30. The spectrometer of claim 29 wherein the means for deriving spectral information includes means for capturing an infrared image.

31. The spectrometer of claim 29 wherein the means for shining is for simultaneously shining infrared light through all of the means for holding, and wherein the means for detecting is for simultaneously detecting infrared light from all of the means for holding.

32. The spectrometer of claim 29 wherein at least one of the means for holding includes a reference means.

33. The spectrometer of claim 29 further including at least one optical fiber in an optical path between the means for shining infrared light and the means for detecting.

34. The spectrometer of claim 29 further including a plurality of optical fibers that are each located in an optical path between at least a portion of the means for shining infrared light and at least a portion of the means for detecting.

35. An infrared spectroscopy method, comprising:
shining infrared light toward contents of a plurality of cells simultaneously located in an instrument, detecting at least a portion of the infrared light after it has interacted with contents of the cells, and
deriving spectral information based on signals derived from the plurality of cells detected in the step of detecting.

36. The method of claim 35 wherein the step of detecting acts on infrared light that has interacted with the plurality of cells by capturing an infrared image.

37. The method of claim 35 wherein the step of shining simultaneously shines infrared light through all of-the cells and wherein the step of detecting simultaneously detects infrared light from all of the cells.

38. The method of claim 35 further including further steps of detecting and deriving for different sample substances in one of the cells and the same reference substance in another of the cells.

39. The method of claim 35 further including further steps of detecting and deriving for different sample substances in one of the cells and a same plurality of different reference substance in others of the cells.

40. The method of claim 35 further including the step of conveying the infrared light with at least one optical fiber.

41. The method of claim 35 further including the step of conveying at least portions of the infrared light with a plurality of optical fibers.

42. An infrared spectroscopy method, comprising:
shining infrared light toward contents of a plurality of cells simultaneously located in an instrument, detecting at least a portion of the infrared light after it has interacted with contents of the cells, and
deriving spectral information based on signals derived from the plurality of cells detected in the step of detecting, wherein one of the plurality of cells includes a sample substance and at least a first and a second of the cells that include different reference substances, and wherein the step of deriving determines a measure of relative quantities in the sample substance of the reference substance in the first cell and the reference substance in the second cell.

43. The method of claim 42 wherein the sample includes a product or an intermediate from a reaction and the first and second reference substances are reagents or intermediates for the reaction.

44. A spectrometer, comprising:
a cell array including a plurality of walls defining a plurality of cavities,
a number of reference samples, each in one of the cavities of the cell array, and
a spatial detector responsive to radiation traveling from an infrared source through contents of a plurality of the cavities.

45. The spectrometer of claim 44 further including at least one optical fiber in an optical path between the infrared source and the spatial detector.

46. The spectrometer of claim 44 further including a plurality of optical fibers that are each located in an optical path between at least a portion of the infrared source and at least one element of the spatial detector.

47. An optical process monitoring instrument, comprising:
a plurality of process feed conduits,
a spatial detector responsive to the feed conduits, and
a signal processor responsive to the spatial detector.

48. The optical process monitoring instrument of claim 47 further including at least one optical fiber and wherein the spatial detector is responsive to at least one of the feed conduits through the optical fiber.

49. The optical process monitoring instrument of claim 47 further including a plurality of optical fibers and wherein the spatial detector is responsive to the feed conduits through the optical fibers.

50. An infrared spectroscopy method, comprising:
shining infrared light toward a plurality of substrate areas simultaneously located in an instrument,
detecting at least a portion of the infrared light after it has interacted with substances located on the substrate areas, and
deriving spectral information based on signals derived from the substances detected in the step of detecting.

51. The method of claim 50 further including the step of conveying the infrared light with at least one optical fiber.

52. The method of claim 50 further including the step of conveying at least portions of the infrared light with a plurality of optical fibers.

53. The method of claim 50 wherein the step of deriving spectral information derives values for a plurality of wavelengths for each of the substances detected in the step of detecting, and further including the step of comparing at least some of the derived values with reference values.

54. A spectrometer, comprising:
an infrared source,
a cell array including a plurality of walls defining a plurality of cavities,
a spectrally selective element,
an infrared spatial detector responsive to infrared radiation traveling from the infrared source through contents of a plurality of the cavities as well as through the spectrally selective element, and
a gasket between the first and second of the walls.

55. A spectrometer, comprising:
an infrared source,
a cell array including a plurality of walls defining a plurality of cavities,
a spectrally selective element, and
an infrared spatial detector responsive to infrared radiation traveling from the infrared source through contents of a plurality of the cavities as well as through the spectrally selective element, wherein the source and detector are arranged relative to the reflective surface of the cell array such that infrared radiation is reflected from the source to the detector without passing through any of the walls.

56. A spectrometer, comprising:

an infrared source, a cell array including a plurality of walls defining a plurality of cavities, a spectrally selective element, an infrared spatial detector responsive to infrared radiation traveling from the infrared source through contents of a plurality of the cavities as well as through the spectrally selective element, and a gasket between the cover and at least the walls defining one of the cells.

57. A spectrometer, comprising:

an infrared source, a cell array including a plurality of walls defining a plurality of cavities, a spectrally selective element, an infrared spatial detector responsive to infrared radiation traveling from the infrared source through contents of a plurality of the cavities as well as through the spectrally selective element, and a purging mechanism for purging a space between at least two of the infrared source, the cell array, and the spatial infrared detector.

58. A spectrometer, comprising:

an infrared source, a cell array including a plurality of walls defining a plurality of cavities, a spectrally selective element, an infrared spatial detector responsive to infrared radiation traveling from the infrared source through contents of a plurality of the cavities as well as through the spectrally selective element, and further including an actuator for moving the cell array.

59. A sample vessel, for a spectrometer comprising:

a plurality of walls defining a plurality of cells, at least one reflecting surface located at one or more of the walls and having at least one optical axis crossing the plurality of cells, wherein the reflecting element is deposited on a top surface of a bottom wall of at least one of the cells in the cell array.

60. A sample vessel, for a spectrometer comprising:

a plurality of walls defining a plurality of cells, and at least one reflecting surface located at one or more of the walls and having at least one optical axis crossing the plurality of cells, wherein the reflective surface is made of aluminum.

61. An infrared spectrometer, comprising:

a plurality of means for holding substances while being simultaneously located in the spectrometer, means for shining infrared light such that it interacts with the substances held by the plurality of means for holding, means for detecting at least a portion of the infrared light after it has interacted with contents of the means for holding substances, means for deriving spectral information based on signals derived from the plurality of cells detected in the step of detecting, and means for purging the means for holding before the step of detecting.

62. An infrared spectrometer, comprising:

a plurality of means for holding substances while being simultaneously located in the spectrometer, means for shining infrared light such that it interacts with the substances held by the plurality of means for holding, means for detecting at least a portion of the infrared light after it has interacted with contents of the means for holding substances, and means for deriving spectral information based on signals derived from the plurality of cells detected in the step of detecting, wherein at least a portion of the means for deriving is for determining whether an infrared spectrum of a sample substance in a first of the means for holding is closer to an infrared spectrum of a reference substance in a second of the means for holding or to an infrared spectrum of a reference substance in a third of the means for holding.

63. An infrared spectroscopy method, comprising:

shining infrared light toward contents of a plurality of cells simultaneously located in an instrument, detecting at least a portion of the infrared light after it has interacted with contents of the cells, deriving spectral information based on signals derived from the plurality of cells detected in the step of detecting, wherein a first of the cells contains a reference substance, wherein a second of the cells contains a sample substance, and wherein the step of deriving compares spectral signals from the reference substance and the sample substance.

64. An infrared spectroscopy method, comprising:

shining infrared light toward contents of a plurality of cells simultaneously located in an instrument, detecting at least a portion of the infrared light after it has interacted with contents of the cells, deriving spectral information based on signals derived from the plurality of cells detected in the step of detecting, and purging the cells before the step of detecting.

65. An infrared spectroscopy method, comprising:

shining infrared light toward contents of a plurality of cells simultaneously located in an instrument, detecting at least a portion of the infrared light after it has interacted with contents of the cells, deriving spectral information based on signals derived from the plurality of cells detected in the step of detecting, wherein one of the plurality of cells includes a sample substance and at least first and second of the cells that include different reference substances, and wherein the step of deriving determines whether an infrared spectrum of the sample substance is closer to an infrared spectrum of the reference substance in the first cell or to an infrared spectrum of the reference substance in the second cell.

66. An infrared spectroscopy method, comprising:

shining infrared light toward contents of a plurality of cells simultaneously located in an instrument, detecting at least a portion of the infrared light after it has interacted with contents of the cells, and deriving spectral information based on signals derived from the plurality of cells detected in the step of detecting, wherein the step of determining includes performing a multivariate spectral analysis.

67. An infrared spectroscopy method, comprising:

shining infrared light toward contents of a plurality of cells simultaneously located in an instrument, detecting at least a portion of the infrared light after it has interacted with contents of the cells, deriving spectral information based on signals derived from the plurality of cells detected in the step of detecting, and changing a process in response to result of the step of determining.

68. A spectrometer, comprising:

a cell array including a plurality of walls defining a plurality of cavities, including an unsealed cavity for a sample, a number of reference samples, each in one of the cavities of the cell array, wherein the cavities of the cell array that include the reference samples are sealed, and a spatial detector responsive to radiation traveling from an infrared source through contents of a plurality of the cavities.

69. A spectrometer, comprising:

a cell array including a plurality of walls defining a plurality of cavities, a number of reference samples, each in one of the cavities of the cell array, a spatial detector responsive to radiation traveling from an infrared source through contents of a plurality of the cavities, and a processor operative to compare spectral information from the number of cavities with spectral information from a sample in a sample cavity.

70. An optical process monitoring instrument, comprising:

a plurality of process feed conduits, wherein at least a first of the conduits is operatively connected to at least a second of the conduits so that contents of the first and second conduits can react, a spatial detector responsive to the feed conduits, and a signal processor responsive to the spatial detector.

71. An infrared spectroscopy method, comprising:

shining infrared light toward a plurality of substrate areas simultaneously located in an instrument, wherein a first of the areas supports a reference substance, wherein a second of the areas contains a sample substance, detecting at least a portion of the infrared light after it has interacted with substances located on the substrate areas, and deriving spectral information based on signals derived from the substances detected in the step of detecting, wherein the step of deriving compares spectral signals from the reference substance and the sample substance.

72. An infrared spectroscopy method, comprising:

shining infrared light toward a plurality of substrate areas simultaneously located in an instrument, detecting at least a portion of the infrared light after it has interacted with substances located on the substrate areas, deriving spectral information based on signals derived from the substances detected in the step of detecting, and purging a volume between the substrate and apparatus used to perform the step of detecting.

73. An infrared spectroscopy method, comprising:

shining infrared light toward a plurality of substrate areas simultaneously located in an instrument, wherein one of the plurality of areas includes a sample substance and at least a first and a second of the areas that include different reference substances, detecting at least a portion of the infrared light after it has interacted with substances located on the substrate areas, and deriving spectral information based on signals derived from the substances detected in the step of detecting, wherein the step of deriving determines whether an infrared spectrum of the sample substance is closer to an infrared spectrum of the reference substance on the first area or to an infrared spectrum of the reference substance on the second area.

74. An infrared spectroscopy method, comprising:

shining infrared light toward a plurality of substrate areas simultaneously located in an instrument, detecting at least a portion of the infrared light after it has interacted with substances located on the substrate areas, and deriving spectral information based on signals derived from the substances detected in the step of detecting, wherein the step of determining includes performing a multivariate spectral analysis.

75. An infrared spectroscopy method, comprising:

shining infrared light toward a plurality of substrate areas simultaneously located in an instrument, detecting at least a portion of the infrared light after it has interacted with substances located on the substrate areas, deriving spectral information based on signals derived from the substances detected in the step of detecting, and initiating a reaction between at least one reagent and the substances on the different areas.

* * * * *